US012778482B2

(12) United States Patent
Zheng et al.

(10) Patent No.: US 12,778,482 B2
(45) Date of Patent: Nov. 3, 2026

(54) SYSTEM FOR PREDICTING ORIGIN POSITION OF VENTRICULAR ARRHYTHMIA, AND ELECTRONIC DEVICE AND STORAGE MEDIUM

(71) Applicants: Jianwei Zheng, Shanghai (CN); Huimin Chu, Zhejiang (CN)

(72) Inventors: Jianwei Zheng, Shanghai (CN); Huimin Chu, Zhejiang (CN)

( * ) Notice: Subject to any disclaimer, the term of this patent is extended or adjusted under 35 U.S.C. 154(b) by 324 days.

(21) Appl. No.: 18/294,867

(22) PCT Filed: Aug. 1, 2022

(86) PCT No.: PCT/CN2022/109360
§ 371 (c)(1),
(2) Date: Feb. 2, 2024

(87) PCT Pub. No.: WO2023/011392
PCT Pub. Date: Feb. 9, 2023

(65) Prior Publication Data

US 2024/0374198 A1 Nov. 14, 2024

(30) Foreign Application Priority Data

Aug. 2, 2021 (CN) ......................... 202110881998.0

(51) Int. Cl.
*A61B 5/00* (2006.01)
*A61B 5/343* (2021.01)
(Continued)

(52) U.S. Cl.
CPC .............. *A61B 5/363* (2021.01); *A61B 5/343* (2021.01); *A61B 5/366* (2021.01); *A61B 5/7203* (2013.01)

(58) Field of Classification Search
CPC ......... A61B 5/363; A61B 5/366; A61B 5/343; A61B 5/7203
See application file for complete search history.

(56) References Cited

U.S. PATENT DOCUMENTS

2004/0230129 A1* 11/2004 Haefner ............. A61N 1/36585 600/510
2008/0221643 A1 9/2008 Olson
(Continued)

FOREIGN PATENT DOCUMENTS

CN 105307565 A 2/2016
CN 105982644 A 10/2016
(Continued)

OTHER PUBLICATIONS

Chen, Genlang et al., A cascaded classifiert for multi-lead ECG based on feature fusion, Computer Methods and Programs in Biomedicine vol. 178, Jun. 20, 2019, pp. 135-143.
(Continued)

*Primary Examiner* — Carl H Layno
*Assistant Examiner* — Aya Ziad Bakkar
(74) *Attorney, Agent, or Firm* — MUNCY, GEISSLER, OLDS & LOWE, P.C.

(57) ABSTRACT

A system for predicting an origin position of a ventricular arrhythmia (VA), an electronic device and a storage medium are disclosed. The system includes an acquisition module (100) for acquiring a body-surface electrocardiogram (ECG) to be subjected to prediction; and a prediction module (200) for performing stage-wise prediction on the body-surface ECG using at least two stages of pre-trained prediction models, thereby obtaining prediction results corresponding to the origin position of the VA. The storage medium stores therein a computer program, which, when executed by a processor, implements the steps of: acquiring a body-surface ECG to be subjected to prediction (S100); and performing stage-wise prediction on the body-surface ECG using at least two stages of pre-trained prediction models, thereby obtaining prediction results corresponding to the origin position of the VA (S200). The electronic device includes the
(Continued)

system and/or the storage medium. They are able to accurately predict the true origin position of a VA among all possible candidates, thereby shortening the time required for a catheter ablation procedure, reducing unnecessary intervention mapping within the heart and reducing complications.

15 Claims, 7 Drawing Sheets

(51) Int. Cl.
*A61B 5/363* (2021.01)
*A61B 5/366* (2021.01)

(56) References Cited

U.S. PATENT DOCUMENTS

| | | | | |
|---|---|---|---|---|
| 2019/0090774 | A1* | 3/2019 | Yang | A61B 5/364 |
| 2019/0365280 | A1 | 12/2019 | Shmayahu et al. | |

FOREIGN PATENT DOCUMENTS

| | | | | | |
|---|---|---|---|---|---|
| CN | 109091138 | A | 12/2018 | | |
| CN | 109259756 | A | 1/2019 | | |
| CN | 109965875 | A | 7/2019 | | |
| CN | 111214225 | A | 6/2020 | | |
| CN | 111680382 | A | 9/2020 | | |
| CN | 111772619 | A | 10/2020 | | |
| CN | 111887836 | A | 11/2020 | | |
| CN | 112450944 | A | 3/2021 | | |
| CN | 113598782 | A | 11/2021 | | |
| EP | 3821801 | A1 | * | 5/2021 | A61B 5/364 |
| WO | WO 2020226534 | A1 | 11/2020 | | |

OTHER PUBLICATIONS

Park Juyoung et al., Cascade Classification with Adaptive Feature Extraction for Arrhythmia Detection, Journal of Medical Systems, vol. 41, No. 1, Nov. 26, 2016, pp. 1-12.

* cited by examiner

SYSTEM FOR PREDICTING ORIGIN POSITION OF VENTRICULAR ARRHYTHMIA, AND ELECTRONIC DEVICE AND STORAGE MEDIUM

TECHNICAL FIELD

The present invention relates to the field of computer technology and, in particular, to a system for predicting an origin position of a ventricular arrhythmia (VA), an electronic device and a storage medium.

BACKGROUND

Ventricular arrhythmias (VAs), including premature ventricular contractions (PVCs) and ventricular tachycardias (VTs), are arrhythmias originating in the ventricles, which are manifested on electrocardiograms (ECGs) as wide QRS complexes. Body-surface ECGs of VA patients show abnormally broad QRS complexes often lasting as long as 0.12 s or longer. VA onsets over an extended period of time tend to bring about changes in the anatomy of the left ventricle and deterioration of the cardiac function. VAs can be found in both patients with organic heart disease and populations of various age groups without organic heart disease, mostly youngsters and middle-aged people.

Catheter ablation can provide effective VA treatment. Before and during an ablation procedure, accurate VA origin localization is very important. In addition, postoperative assessment of ablation efficacy may involve examining consistency of new PVC and VT sites with those prior to the procedure. Although various methods have been proposed based on research studies so far for VA origin localization, all of these remain clinically unsatisfactory in terms of accuracy, sensitivity, specificity and generality because they require mapping of numerous possible VA origin sites by means of 3D modeling used in conjunction with other detection techniques. This can lengthen the surgical time, increase the risk of complications and affect surgical outcomes and prognosis.

It is to be noted that the information disclosed in this Background section is merely intended to provide a better understanding of the general context of the present invention and should not be taken as an acknowledgement or any form of admission that the information forms part of the common general knowledge of those skilled in the art.

SUMMARY OF THE INVENTION

It is an objective of the present invention to provide a system for predicting an origin position of a ventricular arrhythmia (VA), an electronic device and a storage medium, which can accurately predict the true VA origin site among all possible candidates, thereby greatly shortening the time required for a catheter ablation procedure, reducing unnecessary intervention mapping within the heart and reducing patient complications.

To this end, the present invention provides a system for predicting an origin position of a VA, which includes: an acquisition module for acquiring a body-surface ECG to be subjected to prediction; and a prediction module for performing stage-wise prediction on the body-surface ECG using at least two stages of pre-trained prediction models, thereby obtaining prediction results corresponding to the origin position of the VA.

Optionally, the prediction module may include:

a first prediction sub-module for performing a first-stage prediction process on the body-surface ECG using a pre-trained first prediction model, thereby obtaining a first-stage prediction result corresponding to the origin position of the VA;

a second prediction sub-module for performing, based on the first-stage prediction, a second-stage prediction process on the body-surface ECG using a pre-trained second prediction model, thereby obtaining a second-stage prediction result corresponding to the origin position of the VA; and a third prediction sub-module for performing, based on the second-stage prediction, a third-stage prediction process on the body-surface ECG using a pre-trained third prediction model, thereby obtaining a third-stage prediction result corresponding to the origin position of the VA.

Optionally, the prediction module may further include:

a fourth prediction sub-module for performing, based on the third-stage prediction, a fourth-stage prediction process on the body-surface ECG using a pre-trained fourth prediction model, thereby obtaining a fourth-stage prediction result corresponding to the origin position of the VA.

Optionally, the system may further include:

a QRS complex extraction module for determining locations of all QRS complexes and locations of QRS complexes during PVCs or VTs by detecting the body-surface ECG using a pre-trained first machine learning model, wherein:

the first prediction sub-module is configured to perform, based on the locations of the QRS complexes during the PVCs or VTs, the first-stage prediction process on the body-surface ECG using the pre-trained first prediction model, thereby obtaining the first-stage prediction result corresponding to the origin position of the VA;

the second prediction sub-module is configured to perform, based on the locations of the QRS complexes during the PVCs or VTs and the first-stage prediction, the second-stage prediction process on the body-surface ECG using the pre-trained second prediction model, thereby obtaining the second-stage prediction result corresponding to the origin position of the VA;

the third prediction sub-module is configured to perform, based on the locations of the QRS complexes during the PVCs or VTs and the second-stage prediction, the third-stage prediction process on the body-surface ECG using the pre-trained third prediction model, thereby obtaining the third-stage prediction result corresponding to the origin position of the VA; and the fourth prediction sub-module is configured to perform, based on the locations of the QRS complexes during the PVCs or VTs and the third-stage prediction, the fourth-stage prediction process on the body-surface ECG using the pre-trained fourth prediction model, thereby obtaining the fourth-stage prediction result corresponding to the origin position of the VA.

Optionally, the first prediction sub-module may include:

a first extraction unit for extracting a first target ECG portion of a first target length from the body-surface ECG according to the locations of the QRS complexes during the PVCs or VTs; and a first prediction unit for performing the first-stage prediction process on the first target ECG portion using the pre-trained first prediction model, thereby obtaining the first-stage prediction result corresponding to the origin position of the VA.

Additionally or alternatively, the second prediction sub-module may include:

a second extraction unit for extracting a second target ECG portion of a second target length from the body-surface ECG according to the locations of the QRS complexes during the PVCs or VTs; and a second prediction unit for performing, based on the first-stage prediction, the second-stage prediction process on the second target ECG portion using the pre-trained second prediction model, thereby obtaining the second-stage prediction result corresponding to the origin position of the VA.

Additionally or alternatively, the third prediction sub-module may include:

a third extraction unit for extracting a third target ECG portion of a third target length from the body-surface ECG according to the locations of the QRS complexes during the PVCs or VTs; and a third prediction unit for performing, based on the second-stage prediction, the third-stage prediction process on the third target ECG portion using the pre-trained third prediction model, thereby obtaining the third-stage prediction result corresponding to the origin position of the VA.

Additionally or alternatively, the fourth prediction sub-module may include:

a fourth extraction unit for extracting a fourth target ECG portion of a fourth target length from the body-surface ECG according to the locations of the QRS complexes during the PVCs or VTs; and a fourth prediction unit for performing, based on the third-stage prediction, the fourth-stage prediction process on the fourth target ECG portion using the pre-trained fourth prediction model, thereby obtaining the fourth-stage prediction result corresponding to the origin position of the VA.

Optionally, the system may further include:

a first pre-treatment module for determining whether a sampling frequency of the body-surface ECG is equal to a predetermined frequency and, if not, resampling the body-surface ECG.

Optionally, the system may further include:

a second pre-treatment module for denoising the body-surface ECG

Optionally, the second pre-treatment module may be configured to remove high-frequency noise from the body-surface ECG by hierarchical time-frequency resolution and remove low-frequency noise from the body-surface ECG by non-linear fitting.

Optionally, the system may further include: a report generation module for displaying the prediction results corresponding to the origin position of the VA on a pre-defined 3D heart model, thereby generating a 3D prediction report.

To the above end, the present invention also provides a readable storage medium storing therein a computer program, which, when executed by a processor, implements the steps of: acquiring a body-surface ECG to be subjected to prediction; and performing stage-wise prediction on the body-surface ECG using at least two stages of pre-trained prediction models, thereby obtaining prediction results corresponding to the origin position of the VA.

Optionally, performing the stage-wise prediction on the body-surface ECG using the at least two stages of pre-trained prediction models and thereby obtaining the prediction results corresponding to the origin position of the VA may include: performing a first-stage prediction process on the body-surface ECG using a pre-trained first prediction model, thereby obtaining a first-stage prediction result corresponding to the origin position of the VA; performing, based on the first-stage prediction, a second-stage prediction process on the body-surface ECG using a pre-trained second prediction model, thereby obtaining a second-stage prediction result corresponding to the origin position of the VA; and performing, based on the second-stage prediction, a third-stage prediction process on the body-surface ECG using a pre-trained third prediction model, thereby obtaining a third-stage prediction result corresponding to the origin position of the VA.

Optionally, performing the stage-wise prediction on the body-surface ECG using the at least two stages of pre-trained prediction models and thereby obtaining the prediction results corresponding to the origin position of the VA may further include: performing, based on the third-stage prediction, a fourth-stage prediction process on the body-surface ECG using a pre-trained fourth prediction model, thereby obtaining a fourth-stage prediction result corresponding to the origin position of the VA.

Optionally, the computer program, when executed by the processor, may further implement the step of: determining locations of all QRS complexes and locations of QRS complexes during PVCs or VTs by detecting the body-surface ECG using a pre-trained first machine learning model, wherein:

performing the first-stage prediction process on the body-surface ECG using the pre-trained first prediction model includes: performing, based on the locations of the QRS complexes during the PVCs or VTs, the first-stage prediction process on the body-surface ECG using the pre-trained first prediction model;

performing the second-stage prediction process on the body-surface ECG using the pre-trained second prediction model includes: performing, based on the locations of the QRS complexes during the PVCs or VTs and the first-stage prediction, the second-stage prediction process on the body-surface ECG using the pre-trained second prediction model;

performing the third-stage prediction process on the body-surface ECG based on the second-stage prediction using the pre-trained third prediction model includes: performing, based on the locations of the QRS complexes during the PVCs or VTs and the second-stage prediction, the third-stage prediction process on the body-surface ECG using the pre-trained third prediction model; and performing the fourth-stage prediction process on the body-surface ECG based on the third-stage prediction using the pre-trained fourth prediction model includes: performing, based on the locations of the QRS complexes during the PVCs or VTs and the third-stage prediction, the fourth-stage prediction process on the body-surface ECG using the pre-trained fourth prediction model.

Optionally, performing the first-stage prediction process on the body-surface ECG using the pre-trained first prediction model based on the locations of the QRS complexes during the PVCs or VTs may include: extracting a first target ECG portion of a first target length from the body-surface ECG according to the locations of the QRS complexes during the PVCs or VTs; and performing the first-stage prediction process on the first target ECG portion using the pre-trained first prediction model.

Alternatively or additionally, performing the second-stage prediction process on the body-surface ECG using the pre-trained second prediction model based on the locations of the QRS complexes during the PVCs or VTs and the first-stage prediction may include: extracting a second target ECG portion of a second target length from the body-surface ECG according to the locations of the QRS complexes during the PVCs or VTs; and performing, based on the first-stage prediction, the second-stage prediction process on the second target ECG portion using the pre-trained second prediction model, thereby obtaining the second-stage prediction result corresponding to the origin position of the VA.

Alternatively or additionally, performing the third-stage prediction process on the body-surface ECG using the pre-trained third prediction model based on the locations of the QRS complexes during the PVCs or VTs and the second-stage prediction may include: extracting a third target ECG portion of a third target length from the body-surface ECG according to the locations of the QRS complexes during the PVCs or VTs; and performing, based on the second-stage prediction, the third-stage prediction process on the third target ECG portion using the pre-trained third prediction model, thereby obtaining the third-stage prediction result corresponding to the origin position of the VA.

Alternatively or additionally, performing the fourth-stage prediction process on the body-surface ECG using the pre-trained fourth prediction model based on the locations of the QRS complexes during the PVCs or VTs and the third-stage prediction may include: extracting a fourth target ECG portion of a fourth target length from the body-surface ECG according to the locations of the QRS complexes during the PVCs or VTs; and performing, based on the third-stage prediction, the fourth-stage prediction process on the fourth target ECG portion using the pre-trained fourth prediction model, thereby obtaining the fourth-stage prediction result corresponding to the origin position of the VA.

Optionally, the computer program, when executed by the processor, may further implement the step of: displaying the prediction results corresponding to the origin position of the VA on a predefined 3D heart model, thereby generating a 3D prediction report.

Optionally, the computer program, when executed by the processor, may further implement the step of: determining whether a sampling frequency of the body-surface ECG is equal to a predetermined frequency and, if not, resampling the body-surface ECG Optionally, the computer program, when executed by the processor, further implements the step of: denoising the body-surface ECG.

Optionally, denoising the body-surface ECG may include: removing high-frequency noise from the body-surface ECG by hierarchical time-frequency resolution and removing low-frequency noise from the body-surface ECG by nonlinear fitting.

To the above end, the present invention also provides an electronic device including the system as defined above and/or the readable storage medium as defined above.

Compared with the prior art, the system, electronic device and storage medium of the present invention have the advantages as follows: according to the present invention, stage-wise prediction can be carried out on an acquired body-surface ECG to be subjected to prediction by at least two stages of pre-trained prediction models. This enables a stage-wise drilldown search for an origin position of a VA, in which a large region encompassing the VA origin site may be first predicted, and a finer search may be then performed in the region to accurately drill down to a more detailed location encompassing the true VA origin site. In this way, the present invention is able to accurately predict the true VA origin site among all possible VA origin site candidates. This can not only help a physician to rapidly localize a specific target site to be ablated, but can greatly reduce the time required for the catheter ablation procedure, thus reducing unnecessary intervention mapping within the heart, reducing patient complications and providing a basis for assessment after the VA treatment.

LIST OF REFERENCE NUMERALS

Figure 1:
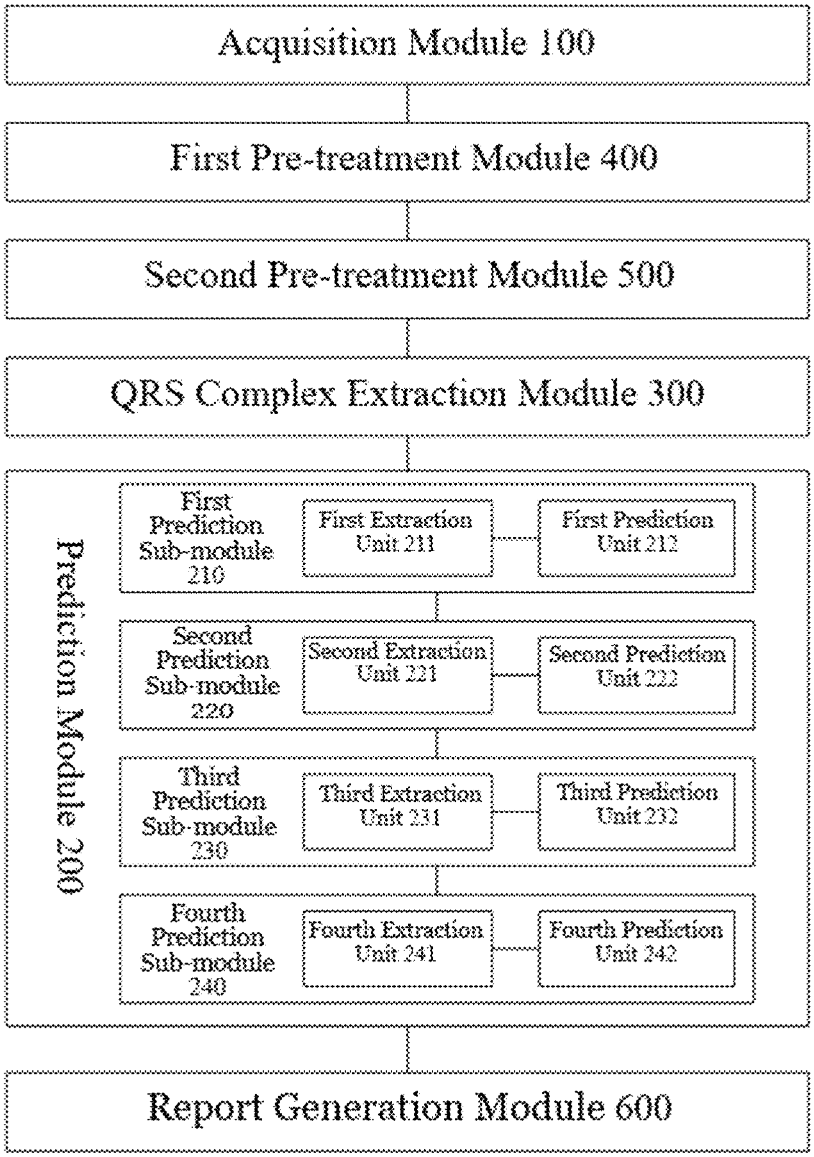
FIG. 1 is a schematic block diagram showing the structure of a system for predicting an origin position of a ventricular arrhythmia (VA) according to an embodiment of the present invention.

100 acquisition module; 200 prediction module; 210 first prediction sub-module; 220 second prediction sub-module; 230 third prediction sub-module; 240 fourth prediction sub-module; 300 QRS complex extraction module; 211 first extraction unit; 212 first prediction unit; 221 second extraction unit; 222 second prediction unit; 231 third extraction unit; 232 third prediction unit; 241 fourth extraction unit; 242 fourth prediction unit; 400 first pre-treatment module; 500 second pre-treatment module; 600 report generation module;

1 left coronary cusp (LCC); 2 right coronary cusp (RCC); 3 aortomitral continuity (AMC); 4 left ventricular summit (LVS); 5 left-right coronary cusp commissure (L-RCC); 6 left His-bundle; 7 mitral valve (MV); 8 left anterior fascicle (LAF); 9 left posterior fascicle (LPF); 10 left anterior papillary muscle (LAPM); 11 left posterior papillary muscle (LPPM); 12 anterior pulmonary cusp (APC); 13 left pulmonary cusp (LPC); 14 right pulmonary cusp (RPC); 15 right ventricular outflow tract (RVOT) anterior septum; 16 RVOT posterior septum; 17 RVOT fee wall; 18 right His-bundle; 19 right anterior papillary muscle (RAPM); 20 tricuspid valve (TV).

DETAILED DESCRIPTION

Systems for predicting an origin position of a ventricular arrhythmia (VA), electronic devices and storage media proposed in the present invention will be described in greater detail below with reference to FIGS. 1 to 9 and to specific embodiments thereof. From the following description, advantages and features of the present invention will become more apparent. It is to be noted that the figures are provided in a very simplified form not necessarily drawn to exact scale and for the only purpose of facilitating easy and clear description of the embodiments. In order that the objects, features and advantages of the present invention can be more apparent and readily understood, reference is to be made to the accompanying drawings. It would be recognized that architectural, proportional, dimensional and other details in the figures are presented only for the purpose of facilitating, in conjunction with the disclosure herein, the understanding and reading of those familiar with the art, rather than being intended to limit conditions under which the present invention can be implemented. Therefore, any and all architectural modifications, proportional variations or dimensional changes that achieve the same or similar benefits and objects as the present invention are considered to fall within the scope of the teachings herein.

It is to be noted that, as used herein, relational terms such as first and second, etc., are only used to distinguish one entity or operation from another entity or operation, and do not necessarily require or imply these entities having such an order or sequence. Moreover, the terms "comprise," "include," or any other variations thereof are intended to cover a non-exclusive inclusion within a process, method, article, or apparatus that comprises a list of elements including not only those elements but also those that are not explicitly listed, or other elements that are inherent to such processes, methods, goods, or equipment. In the case of no more limitation, the element defined by the sentence "includes a . . . " does not exclude the existence of another identical element in the process, the method, or the device including the element.

In principle, the present invention seeks to provide a system for predicting an origin position of a ventricular arrhythmia (VA), an electronic device and a storage medium, which can accurately predict the true VA origin site among all possible candidates, thereby greatly shortening the time required for a catheter ablation procedure, reducing unnecessary intervention mapping within the heart and reducing patient complications. It is to be noted that the present invention is not directed to a method for disease diagnosis or treatment, but is intended merely to provide a prediction relating to all possible VA origin site candidates. Based on the prediction, a physician can determine the true origin of a VA in the patient.

It is to be noted that systems for predicting an origin position of a VA according to embodiments of the present invention can be configured on electronic devices, which may be personal computers, mobile terminals or the like. The mobile terminals may be hardware devices running various operating systems (OS), such as mobile phones and tablet computers.

In order to achieve the above goal, the present invention provides a system for predicting an origin position of a ventricular arrhythmia (VA). Reference is now made to FIG. 1, a schematic block diagram showing the structure of a system for predicting an origin position of a VA according to an embodiment of the present invention. As shown in FIG. 1, the system includes an acquisition module 100 and a prediction module 200. The acquisition module 100 is used to acquire a body-surface electrocardiogram (ECG) to be subjected to prediction, and the prediction module 200 is configured to perform stage-wise prediction on the body-surface ECG using at least two stages of pre-trained prediction models to give a VA origin site prediction. Thus, according to the present invention, the stage-wise prediction performed on the acquired body-surface ECG by the at least two stages of pre-trained prediction models enables a stage-wise drilldown search for the origin position of the VA. Specifically, a large region encompassing the VA origin site may be first predicted, and a finer search may be then performed in the region to drill down to a more detailed location encompassing the VA origin site. In this way, the present invention is able to accurately predict the true VA origin site among all possible VA origin site candidates. This can not only help a physician to rapidly localize a specific target site to be ablated, but can greatly reduce the time required for the catheter ablation procedure, thus reducing unnecessary intervention mapping within the heart, reducing patient complications and providing a basis for assessment after the VA treatment.

Specifically, the acquired body-surface ECG to be subjected to prediction may be a 12-lead body-surface ECG (obtained with six limb leads (I, II, III, AVR, aVL and aVF) and six chest leads (V1 to V6)).

As shown in FIG. 1, the system may further include a first pre-treatment module 400, the first pre-treatment module 400 is used for determining whether a sampling frequency of the body-surface ECG is equal to a predetermined frequency. If not, the body-surface ECG may be resampled. Accordingly, the prediction module 200 may be configured to perform the stage-wise prediction on the resampled body-surface ECG by the at least two stages of pre-trained prediction models. As such, if the sampling frequency of the acquired body-surface ECG is not equal to the predetermined frequency, the body-surface ECG may be resampled, thus tuning its sampling frequency to the predetermined frequency. In this way, more details can be obtained from the body-surface ECG, providing a sound foundation for subsequent accurate VA origin site prediction. Specifically, if the sampling frequency of the acquired body-surface ECG is higher than the predetermined frequency, the body-surface ECG may be downsampled to lower its sampling frequency to the predetermined frequency. If the sampling frequency of the acquired body-surface ECG is lower than the predetermined frequency, the body-surface ECG may be upsampled to raise its sampling frequency to the predetermined frequency. The predetermined frequency may be set, as required. As a non-limiting example, the predetermined frequency may be set to 2000 Hz.

In one exemplary embodiment, as shown in FIG. 1, the system may further include a second pre-treatment module 500, the second pre-treatment module 500 is used for performing a denoising process on the body-surface ECG. The denoising process performed on the body-surface ECG can effectively remove noise therefrom, additionally enhancing the prediction accuracy of the inventive system. Preferably, the second pre-treatment module 500 is configured to denoise the body-surface ECG, which sampling frequency has been lowered or raised to the predetermined frequency.

Specifically, the second pre-treatment module 500 may be configured to remove high-frequency noise from the body-surface ECG (which sampling frequency has been preferably raised or lowered to the predetermined frequency) by hierarchical time-frequency resolution and remove low-frequency noise from the body-surface ECG (which sampling frequency has been preferably raised or lowered to the predetermined frequency) by non-linear fitting. Through using the combination of hierarchical time-frequency resolution and non-linear fitting for denoising, noise can be effectively removed from the body-surface ECG (which sampling frequency has been preferably raised or lowered to the predetermined frequency), resulting in a smooth signal required by the subsequent analysis, which can additionally enhance the prediction accuracy of the inventive system.

Preferably, as shown in FIG. 1, the prediction module 200 may include a first prediction sub-module 210, a second prediction sub-module 220 and a third prediction sub-module 230. The first prediction sub-module 210 may be configured to perform a first-stage prediction process on the body-surface ECG (which has preferably been denoised) using a pre-trained first prediction model, thereby obtaining a first-stage prediction result corresponding to the origin position of the VA. The second prediction sub-module 220 may be configured to, based on the first-stage prediction, perform a second-stage prediction process on the body-surface ECG (which has preferably been denoised) using a pre-trained second prediction model, obtaining a second-stage prediction result corresponding to the origin position of the VA. The third prediction sub-module 230 may be configured to, based on the second-stage prediction, perform a third-stage prediction process on the body-surface ECG (which has preferably been denoised) using the pre-trained third prediction model, obtaining a third-stage prediction result corresponding to the origin position of the VA. In this way, a three-stage prediction scheme is established with the first, second and third prediction models, in which the first-stage prediction obtained from the first prediction model serves as a basis for the next-stage prediction process (i.e., the second-stage prediction process) performed by the second prediction model, and the second-stage prediction obtained from the second prediction model serves as a basis for the next-stage prediction process (i.e., the third-stage prediction process) performed by the third prediction model. Finally, the third-stage prediction is obtained. This stage-wise prediction technique with incremental drilldown and refinement capabilities can provide a more accurate final prediction result corresponding to the origin position of the VA with substantially reduced prediction errors.

As shown in FIG. 1, the prediction module 200 may further include a fourth prediction sub-module 240, the fourth prediction sub-module 240 is configured to, based on the third-stage prediction, perform a fourth-stage prediction process on the body-surface ECG (which has preferably been denoised) using a pre-trained fourth prediction model, obtaining a fourth-stage prediction result corresponding to the origin position of the VA. In this way, the third-stage prediction serves as a basis for the next-stage prediction process (i.e., the fourth-stage prediction process) performed by the fourth prediction model, thereby obtaining a more detailed VA origin site prediction, which further facilitates rapid identification of a specific target ablation site by a physician and can additionally help in reducing the time required by the catheter ablation procedure.

Reference is now made to Table 1 below, which summarizes anatomical regions that can be predicted as VA origin site candidates in a four-stage prediction process according to the present invention. As shown in Table 1, a first-stage prediction process can produce a first-stage VA origin site prediction, which may identify the left ventricle (LV), the right ventricle (RV) and the epicardium as candidate sites. A second-stage prediction process can produce a second-stage VA origin site prediction, which may identify the left ventricular outflow tract (LVOT), a left ventricular non-outflow tract region, the RVOT, a right ventricular non-outflow tract region and the epicardium, as candidate sites. A third-stage prediction process can produce a third-stage VA origin site prediction, which may identify the LCC, RCC, AMC, LVS, L-RCC, left His-bundle, MV, left ventricular septum (LVS), papillary muscles (PM), APC, LPC, RPC, RVOT septum, RVOT fee wall, right His-bundle, tricuspid valve (TV), right anterior PM (APM) and epicardium, as candidate sites. A fourth-stage prediction process can produce a fourth-stage VA origin site prediction, which may identify the LCC, RCC, AMC, LVS, L-RCC, left His-bundle, MV, LAF, LPF, LAPM, LPPM, APC, LPC, RPC, RVOT posterior septum, RVOT anterior septum, RVOT fee wall, right His-bundle, TV, RAPM and epicardium, as candidate sites. Thus, according to the present invention, a stage-wise prediction result corresponding to the origin position of the VA scheme with incremental drilldown and refinement capabilities can be established with four prediction models, which can encompass a total of 21 VA origin site candidates, covering all the common VA origin sites. According to the present invention, the first prediction model provides prediction accuracy exceeding 99% regarding the LV and RV, and the second prediction model provides prediction accuracy exceeding 99% regarding outflow tract and non-outflow tract regions.

TABLE 1

Anatomical Regions Predictable by Four-Stage Prediction Scheme as Candidate VA Origin Sites

| | First-stage prediction | Second-stage prediction | Third-stage prediction | Fourth-stage prediction |
|---|---|---|---|---|
| Anatomical regions | LV | LVOT | LCC | LCC |
| | | | RCC | RCC |
| | | | AMC | AMC |
| | | | LVS | LVS |
| | | | L-RCC | L-RCC |
| | | Left ventricular non-outflow tract region | Left His-bundle | Left His-bundle |
| | | | MV | MV |
| | | | LVS | LAF |
| | | | | LPF |
| | | | PM | LAPM |
| | | | | LPPM |
| | RV | RVOT | APC | APC |
| | | | LPC | LPC |
| | | | RPC | RPC |

TABLE 1-continued

| Anatomical Regions Predictable by Four-Stage Prediction Scheme as Candidate VA Origin Sites | | | |
|---|---|---|---|
| First-stage prediction | Second-stage prediction | Third-stage prediction | Fourth-stage prediction |
| | | RVOT septum | RVOT posterior septum |
| | | | RVOT anterior septum |
| | | RVOT fee wall | RVOT fee wall |
| | Right ventricular non-outflow tract region | Right His-bundle | Right His-bundle |
| | | TV | TV |
| | | RAPM | RAPM |
| Epicardium | Epicardium | Epicardium | Epicardium |

Preferably, as shown in FIG. 1, the system may further include a QRS complex extraction module 300, the QRS complex extraction module 300 is configured to detect the body-surface ECG (which has preferably been denoised) with a pre-trained first machine learning model to determine locations of all QRS complexes and locations of QRS complexes during premature ventricular contractions (PVCs) or ventricular tachycardias (VTs). Accordingly, the first prediction sub-module 210 may be configured to, based on the locations of the QRS complexes during the PVCs or VTs, perform the first-stage prediction process on the body-surface ECG (which has preferably been denoised) using the pre-trained first prediction model, thereby obtaining the first-stage prediction result corresponding to the origin position of the VA. The second prediction sub-module 220 may be configured to, based on both the locations of the QRS complexes during the PVCs or VTs and the first-stage prediction, perform the second-stage prediction process on the body-surface ECG (which has preferably been denoised) using the pre-trained second prediction model, thereby obtaining the second-stage prediction result corresponding to the origin position of the VA. The third prediction sub-module 230 may be configured to, based on both the locations of the QRS complexes during the PVCs or VTs and the second-stage prediction, perform the third-stage prediction process on the body-surface ECG (which has preferably been denoised) using the pre-trained third prediction model, thereby obtaining the third-stage prediction result corresponding to the origin position of the VA. The fourth prediction sub-module 240 may be configured to, based on both the locations of the QRS complexes during the PVCs or VTs and the third-stage prediction, perform the fourth-stage prediction process on the body-surface ECG (which has preferably been denoised) using the pre-trained fourth prediction model, thereby obtaining the fourth-stage prediction result corresponding to the origin position of the VA.

Figure 2:
FIG. 2 schematically illustrates a specific example of labeled QRS complexes during PVCs or VTs.

Since the body-surface ECG may be displayed for tens of seconds to one hour in each cycle, detecting it with the pre-trained first machine learning model allows quick extraction of QRS complexes during PVCs or VTs, resulting in time savings and reducing the physician's work load. Moreover, it can avoid the proneness to errors that may arise from manual detection of QRS complexes during PVCs or VTs. Reference is made to FIG. 2, which schematically illustrates a specific example of labeled QRS complexes during PVCs or VTs. As shown in FIG. 2, in this specific example, a total of 7 positive QRS complexes during PVCs or VTs are labeled on the body-surface ECG, and the locations of the QRS complexes are represented by those of their peaks. Notably, as would be appreciated by those skilled in the art, in some other embodiments, the QRS complexes may be negative, and the locations of them may be accordingly represented by those of their troughs.

Additionally, as shown in FIG. 1, the first prediction sub-module 210 may include:

- a first extraction unit 211, configured to, based on the locations of the QRS complexes during the PVCs or VTs, extract a first target ECG portion of a first target length from the body-surface ECG (which has preferably been denoised); and
- a first prediction unit 212 configured to perform the first-stage prediction process on the first target ECG portion using the pre-trained first prediction model, thereby obtaining the first-stage prediction result corresponding to the origin position of the VA.

Specifically, according to the first target length, the location of one of the QRS complexes during the PVCs or VTs may be taken as a reference point, and the first target ECG portion of the first target length may be extracted from the body-surface ECG (which has preferably been denoised) so as to partially precede and partially succeed the reference point. The first target ECG portion may encompass all the data points required by the first prediction model to accurately predict a first-level anatomical region encompassing the origin position of the VA. As an example, if the first target length encompasses $a_1$ data points, then with the location of one of the QRS complexes during the PVCs or VTs being taken as a reference point, $(a_1-1)/2$ data points preceding the reference point and $(a_1+1)/2$ data points succeeding the reference point, or $(a_1+1)/2$ data points preceding the reference point and $(a_1-1)/2$ data points succeeding the reference point, may be extracted. For example, if the sampling frequency of the denoised body-surface ECG is 2000 Hz, the first target length may preferably encompass 250 data points (corresponding to 0.125 seconds).

As shown in FIG. 1, the second prediction sub-module 220 may include:

- a second extraction unit 221 configured to, based on the locations of the QRS complexes during the PVCs or VTs, extract a second target ECG portion of a second target length from the body-surface ECG (which has preferably been denoised); and
- a second prediction unit 222 configured to, based on the first-stage prediction, perform the second-stage prediction process on the second target ECG portion using the pre-trained second prediction model, thereby obtaining the second-stage prediction result corresponding to the origin position of the VA.

Specifically, according to the second target length, the location of one of the QRS complexes during the PVCs or VTs may be taken as a reference point, and the second target ECG portion of the second target length may be extracted from the body-surface ECG (which has preferably been denoised) so as to partially precede and partially succeed the reference point. The second target ECG portion may encompass all the data points required by the second prediction model to accurately predict a second-level anatomical region encompassing the origin position of the VA. As an example, if the second target length encompasses $a_2$ data points, then with the location of one of the QRS complexes during the PVCs or VTs being taken as a reference point, $(a_2-1)/2$ data points preceding the reference point and $(a_2+1)/2$ data points succeeding the reference point, or $(a_2+1)/2$ data points preceding the reference point and $(a_2-1)/2$ data points succeeding the reference point, may be extracted. For example, if the sampling frequency of the denoised body-surface ECG is 2000 Hz, the second target length may preferably encompass 550 data points (corresponding to 0.275 seconds).

The third prediction sub-module 230 may include:

- a third extraction unit 231 configured to, based on the locations of the QRS complexes during the PVCs or VTs, extract a third target ECG portion of a third target length from the body-surface ECG (which has preferably been denoised); and
- a third prediction unit 232 configured to, based on the second-stage prediction, perform the third-stage prediction process on the third target ECG portion using the pre-trained third prediction model, thereby obtaining the third-stage prediction result corresponding to the origin position of the VA.

Specifically, according to the third target length, the location of one of the QRS complexes during the PVCs or VTs may be taken as a reference point, and the third target ECG portion of the third target length may be extracted from the body-surface ECG (which has preferably been denoised) so as to partially precede and partially succeed the reference point. The third target ECG portion may encompass all the data points required by the third prediction model to accurately predict a third-level anatomical region encompassing the origin position of the VA. As an example, if the third target length encompasses $a_3$ data points, then with the location of one of the QRS complexes during the PVCs or VTs being taken as a reference point, $(a_3-1)/2$ data points preceding the reference point and $(a_3+1)/2$ data points succeeding the reference point, or $(a_3+1)/2$ data points preceding the reference point and $(a_3-1)/2$ data points succeeding the reference point, may be extracted. For example, if the sampling frequency of the denoised body-surface ECG is 2000 Hz, the third target length may preferably encompass 360 data points (corresponding to 0.18 seconds).

The fourth prediction sub-module 240 may include:

- a fourth extraction unit 241 configured to, based on the locations of the QRS complexes during the PVCs or VTs, extract a fourth target ECG portion of a fourth target length from the body-surface ECG (which has preferably been denoised); and
- a fourth prediction unit 242 configured to, based on the third-stage prediction, perform the fourth-stage prediction process on the fourth target ECG portion using the pre-trained fourth prediction model, thereby obtaining the fourth-stage prediction result corresponding to the origin position of the VA.

Specifically, according to the fourth target length, the location of one of the QRS complexes during the PVCs or VTs may be taken as a reference point, and the fourth target ECG portion of the fourth target length may be extracted from the body-surface ECG (which has preferably been denoised) so as to partially precede and partially succeed the reference point. The fourth target ECG portion may encompass all the data points required by the fourth prediction model to accurately predict a fourth-level anatomical region encompassing the origin position of the VA. As an example, if the fourth target length encompasses $a_4$ data points, then with the location of one of the QRS complexes during the PVCs or VTs being taken as a reference point, $(a_4-1)/2$ data points preceding the reference point and $(a_4+1)/2$ data points succeeding the reference point, or $(a_4+1)/2$ data points preceding the reference point and $(a_4-1)/2$ data points succeeding the reference point, may be extracted. For example, if the sampling frequency of the denoised body-surface ECG is 2000 Hz, the fourth target length may preferably encompass 320 data points (corresponding to 0.16 seconds).

Figure 3:
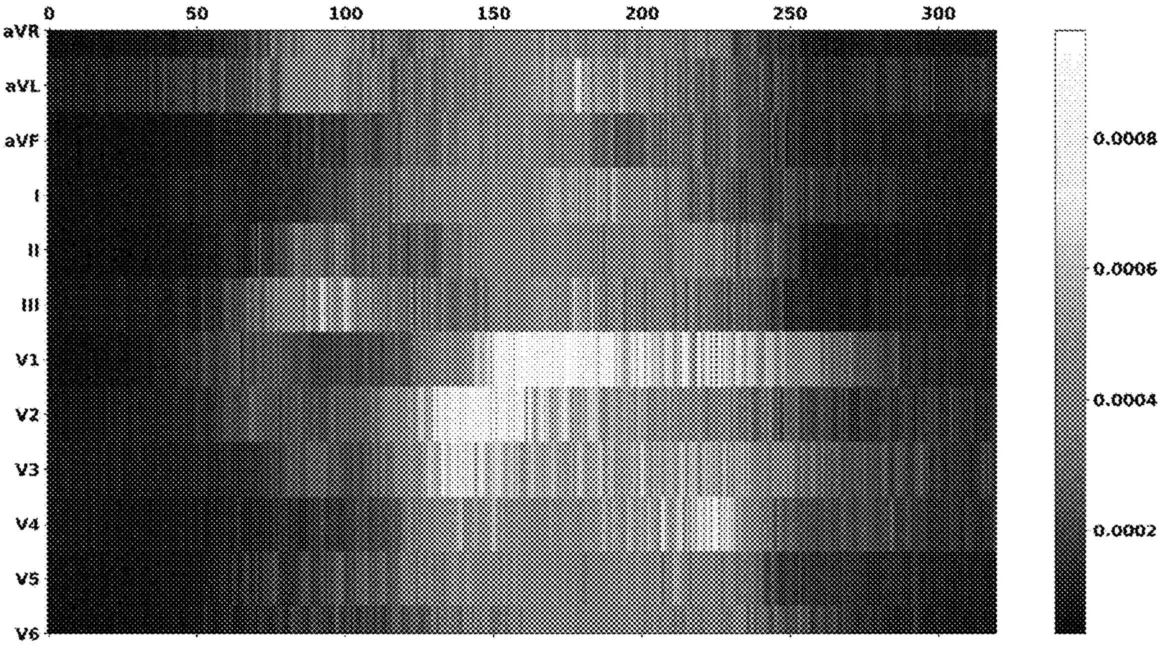
FIG. 3 illustrates a frequency spectrum showing significance of each lead to a VA origin site.

FIG. 3 schematically illustrates a frequency spectrum showing significance of each lead of the body-surface ECG to the origin position of the VA, in which the abscissas represents the data points in the fourth target ECG portion, and the ordinates represent the leads. A data point with greater brightness is more significant to the origin position of the VA. As shown in FIG. 3, the V1 lead is most significant to the origin position of the VA, and among the data points from the V1 lead, the $150^{th}$ to $200^{th}$ data points have the greatest significance.

Figure 4:
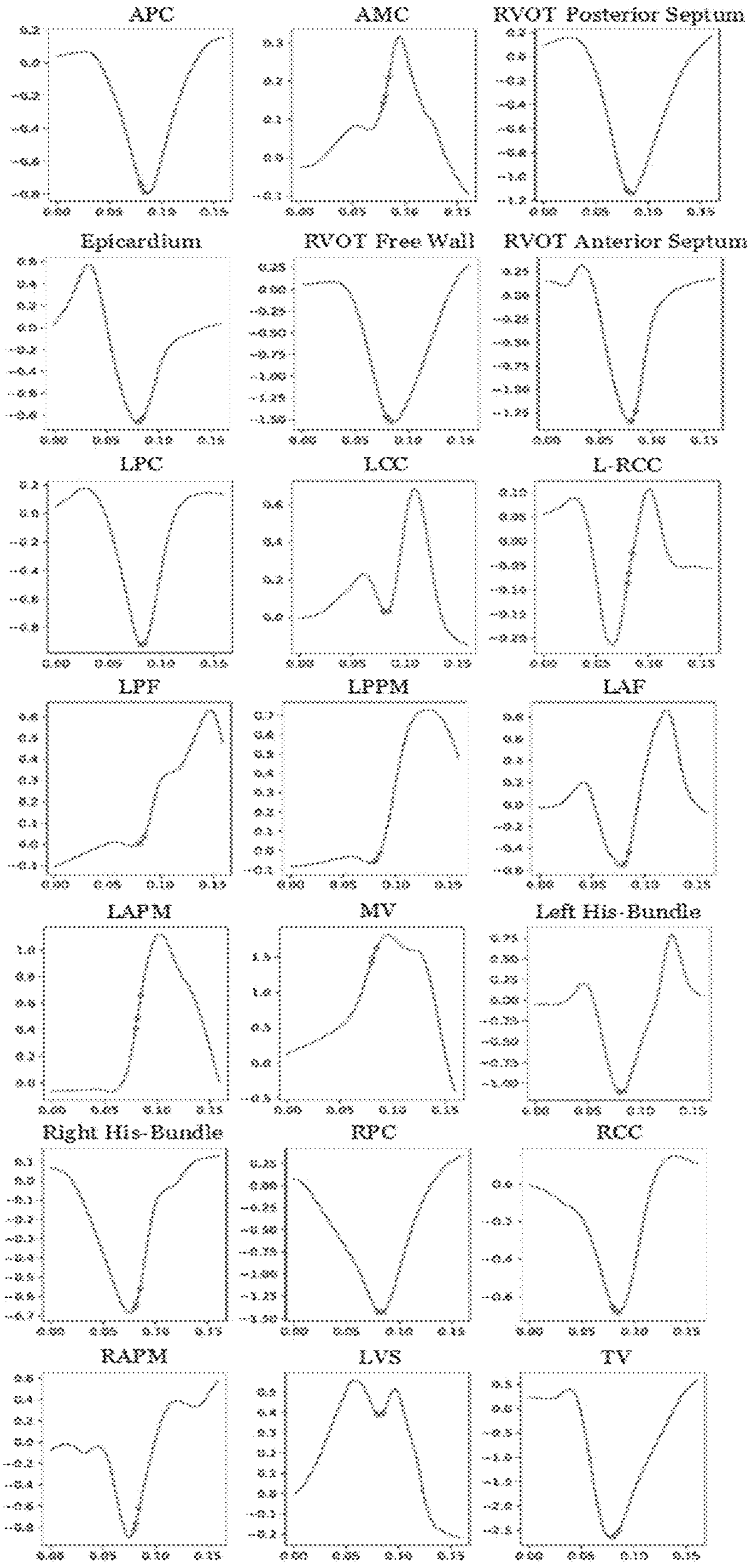
FIG. 4 schematically shows significant data points for decision-making in averaged ECG traces from the V1 lead at different arrhythmogenic origin sites.

Reference is additionally made to FIG. 4, which schematically shows significant data points for decision-making in averaged ECG traces from the V1 lead at different arrhythmogenic original sites, in which the vertical axis represents voltage measured in millivolts (mV) and the horizontal axis represents time measured in seconds(s). As shown in FIG. 4, the different arrhythmogenic original sites are associated with different significant data points for decision-making. The fourth prediction model may perform a feature extraction process on the fourth target ECG portion (for extracting such significant data points for decision-making) and predict the origin position of the VA based on the extracted significant data points. Notably, as would be appreciated by those skilled in the art, the averaged ECG traces from the V1 lead at the various arrhythmogenic original sites are obtained by averaging fourth target ECG portions corresponding to the arrhythmogenic original sites. For example, the averaged ECG trace at the APC from the V1 lead is obtained by averaging fourth target ECG portions of various body-surface ECGs obtained at the APC when it is identified as the origin position of the VA.

Figure 5:
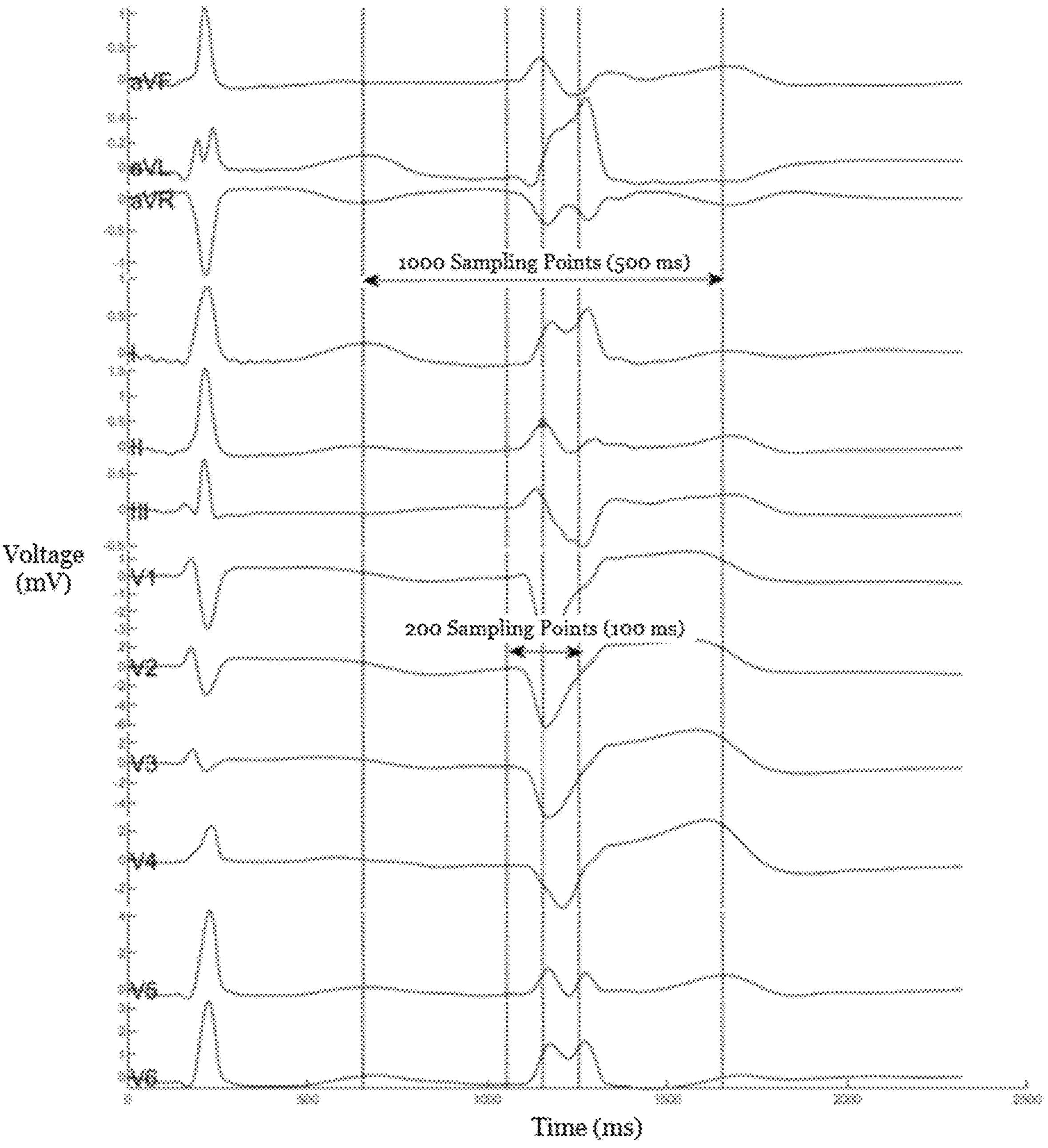
FIG. 5 schematically illustrates an automatic search for an optimal output length for an ECG portion according to an embodiment of the present invention.

Preferably, the first, second, third and fourth target lengths may be determined by a grid search performed by a pre-trained second machine learning model on numerous body-surface ECGs (which sampling frequencies have also been adjusted to the predetermined frequency, e.g., 2000 Hz), in which QRS complexes during PVCs or VTs have been labeled. According to the present invention, from the search performed by the pre-trained second machine learning model, optimal input lengths for the first, second, third and fourth prediction models can be obtained automatically. This can enhance prediction accuracy of each prediction model while taking into account their computational burden. Reference is now made to FIG. 5, which schematically illustrates an automatic search for an optimal output length for an ECG portion according to an embodiment of the present invention. As shown in FIG. 5, in practical operation, the second machine learning model may perform a search within a predetermined candidate input length range at a predetermined step (e.g., 5 ms). The candidate input length range may be determined, as required. For example, if the sampling frequency of the body-surface ECG is 2000 Hz, the candidate input length range may be set to 200 to 1000 data points, i.e., 100 ms to 500 ms.

Figure 6:
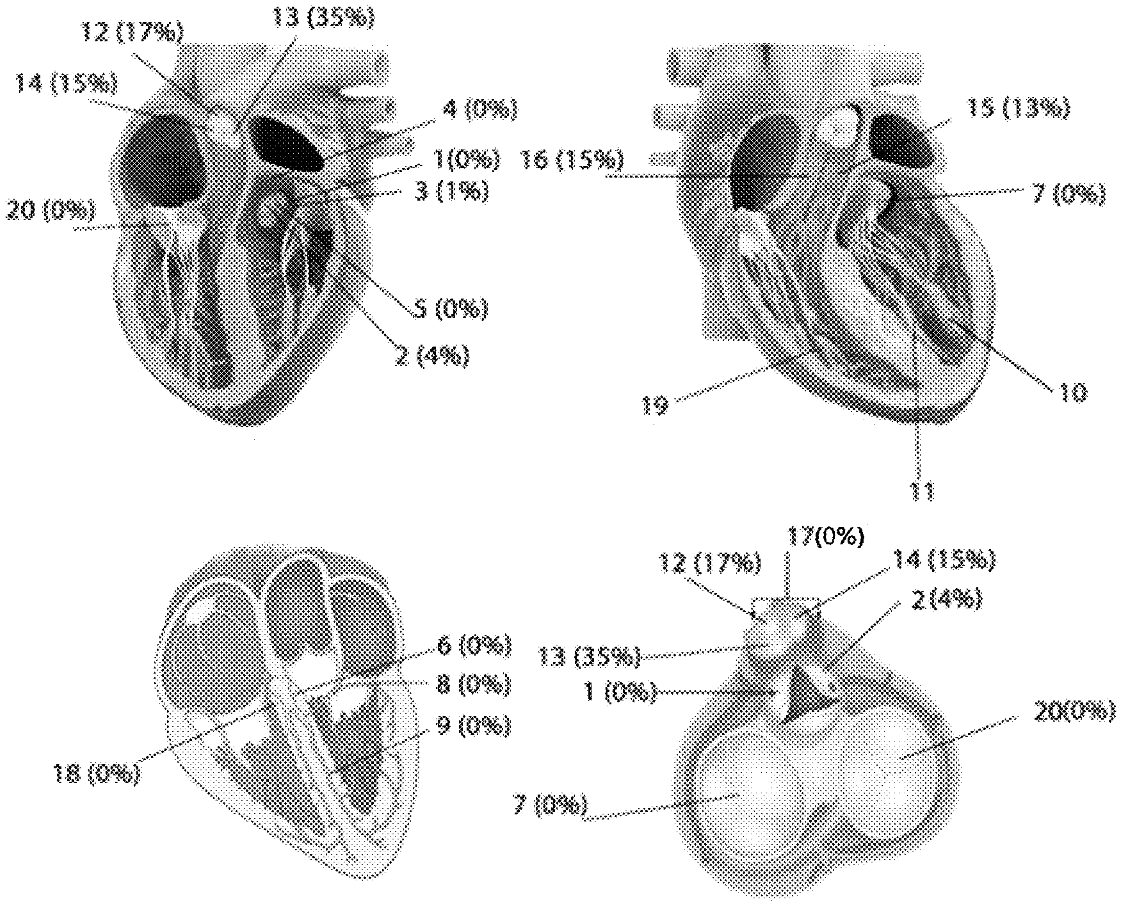
FIG. 6 is a schematic illustration of a specific example of displayed prediction results corresponding to the origin position of the VA.

Preferably, as shown in FIG. 1, the system may further include a report generation module 600, the report generation module 600 is configured to display the prediction results corresponding to the origin position of the VA on a predefined three-dimensional (3D) heart model, as a 3D prediction report. Through displaying the prediction results corresponding to the origin position of the VA on the predefined 3D heart model, the predictions can be presented to a physician more intuitively, facilitating his/her reading. The system of the present invention can ultimately predict a probability for each of the common arrhythmogenic original sites, and the physician can determine the true arrhythmogenic original site based on the predicted probabilities for the candidate arrhythmogenic original sites. Reference is now made to FIG. 6, a schematic illustration of a specific example of the displayed prediction results corresponding to the origin position of the VA. As shown in FIG. 6, in this specific example, location 13 (LPC) is predicted with the highest probability of being the arrhythmogenic original site, indicating that this location is most likely to be the arrhythmogenic original site. Location 12 (APC) is predicted with the second highest probability of being the arrhythmogenic original site, indicating that this location is second-most likely to be the arrhythmogenic original site. Locations 14 (APC) and 16 (RVOT posterior septum) are predicted with the third highest probability of being the arrhythmogenic original site, indicating that these locations are third-most likely to be the arrhythmogenic original site. Location 15 (RVOT anterior septum) is predicted with the fourth highest probability of being the arrhythmogenic original site, indicating that this location is fourth-most likely to be the arrhythmogenic original site. Location 2 (RCC) is predicted with the fifth highest probability of being the arrhythmogenic original site, indicating that this location is fifth-most likely to be the arrhythmogenic original site. Location 3 (AMC) is predicted with the sixth highest probability of being the arrhythmogenic original site, indicating that this location is sixth-most likely to be the arrhythmogenic original site. The predicted probabilities for locations 1 (LCC), 4 (LVS), 5 (L-RCC), 6 (left His-bundle), 7 (MV), 8 (LAF), 9 (LPF), 10 (LAPM), 11 (LPPM), 17 (RVOT fee wall), 18 (right His-bundle), 19 (RAPM) and 20 (TV) and for the epicardium (not shown) are all zero, indicating that it is unlikely for any of these locations to be the arrhythmogenic original site.

Figure 7:
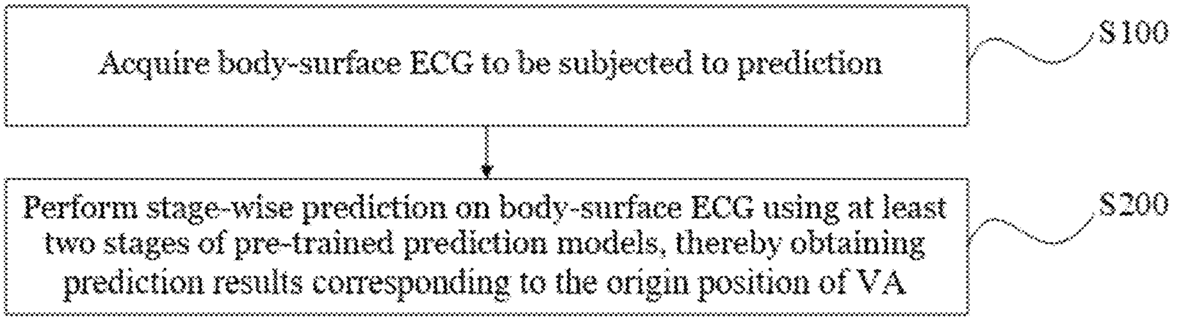
FIG. 7 is a schematic flowchart of a method for predicting an origin position of a VA according to an embodiment of the present invention.

The present invention also provides a method for predicting an origin position of a VA, which corresponds to the above-discussed system. FIG. 7 is a schematic flowchart of a method for predicting an origin position of a VA according to an embodiment of the present invention. As shown in FIG. 7, the method includes the steps of:

Step S100: acquiring a body-surface ECG to be subjected to prediction; and

Step S200: performing stage-wise prediction on the body-surface ECG using at least two stages of pre-trained prediction models, thereby obtaining prediction results corresponding to the origin position of the VA.

Thus, according to the present invention, the stage-wise prediction performed on the acquired body-surface ECG by the at least two stages of pre-trained prediction models enables a stage-wise drilldown search for the origin position of the VA. Specifically, a large region encompassing the VA origin site may be first predicted, and a finer search may be then performed in the region to drill down to a more detailed location encompassing the VA origin site. In this way, the present invention is able to accurately predict the true VA origin site among all possible VA origin site candidates. This can not only help a physician to rapidly localize a specific target site to be ablated, but can greatly reduce the time required for the catheter ablation procedure, thus reducing unnecessary intervention mapping within the heart, reducing patient complications and providing a basis for assessment after the VA treatment.

Figure 8:
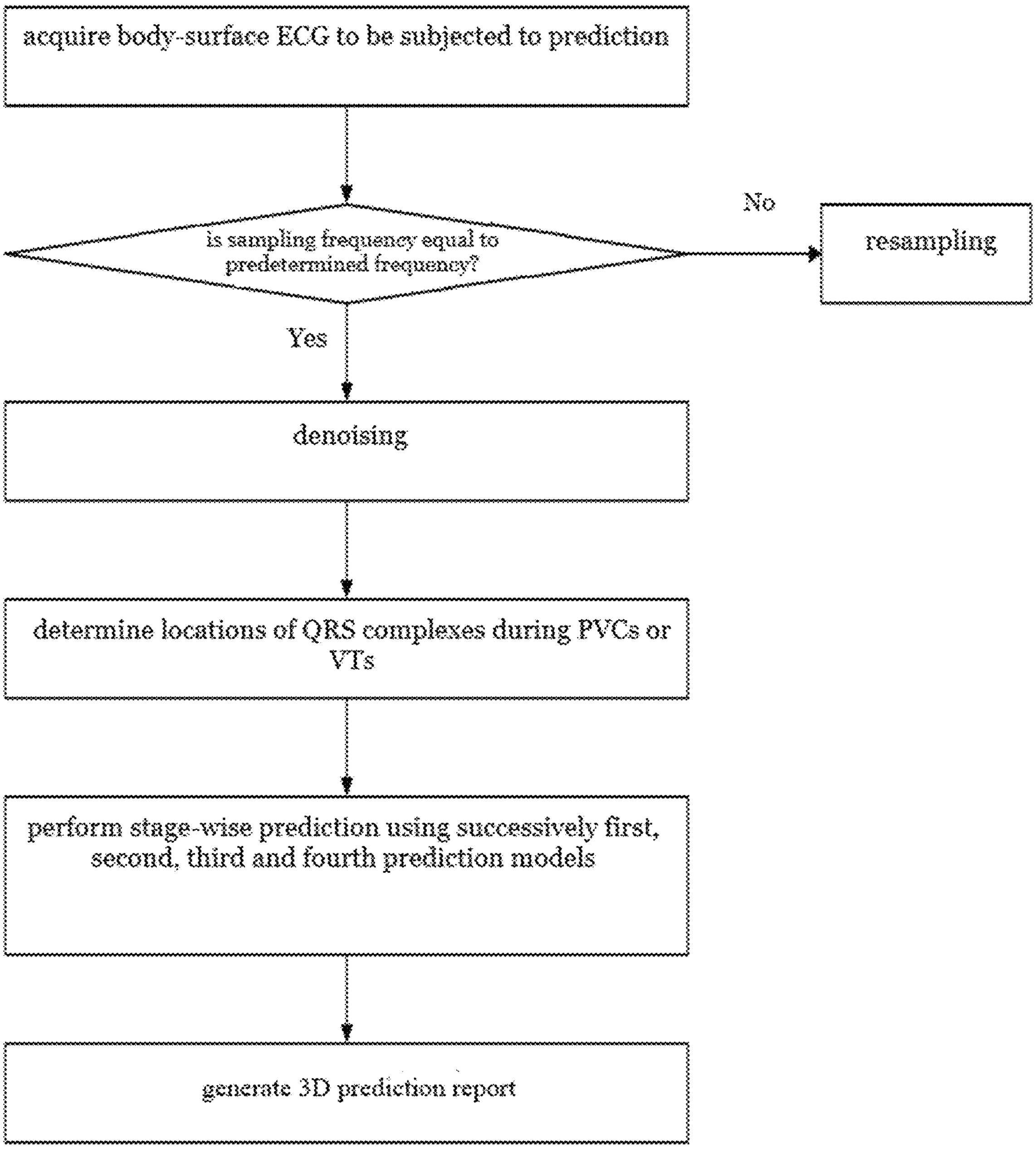
FIG. 8 is a schematic flowchart of a detailed process for predicting an origin position of a VA according to an embodiment of the present invention.

Additional reference is made to FIG. 8, a schematic flowchart of a detailed process for predicting an origin position of a VA according to an embodiment of the present invention. As shown in FIG. 8, before the stage-wise prediction is performed on the body-surface ECG using the at least two stages of pre-trained prediction models to produce the prediction results corresponding to the origin position of the VA, the method may further include:

determining whether a sampling frequency of the body-surface ECG is equal to a predetermined frequency, and if not, resampling the body-surface ECG.

As such, if the sampling frequency of the acquired body-surface ECG is not equal to the predetermined frequency, the body-surface ECG may be resampled (upsampled or downsampled), thus tuning its sampling frequency to the predetermined frequency. In this way, more details can be obtained from the body-surface ECG, providing a sound foundation for subsequent accurate VA origin site prediction.

Further, as shown in FIG. 8, before the stage-wise prediction is performed on the body-surface ECG using the at least two stages of pre-trained prediction models to produce the prediction results corresponding to the origin position of the VA, the method may further include:

denoising the body-surface ECG (which has preferably been resampled).

In this way, through denoising the body-surface ECG (which has preferably been resampled), noise can be effectively removed therefrom, providing a sounder foundation for subsequent accurate VA origin site prediction.

Specifically, denoising the body-surface ECG may include:

removing high-frequency noise from the body-surface ECG by hierarchical time-frequency resolution and removing low-frequency noise from the body-surface ECG by non-linear fitting.

Through using the combination of hierarchical time-frequency resolution and non-linear fitting for denoising, noise can be effectively removed from the body-surface ECG (which sampling frequency has been preferably raised or lowered to the predetermined frequency), resulting in a smooth signal required by the subsequent analysis, which can additionally enhance the arrhythmia site prediction accuracy of the inventive method.

With continued reference to FIG. 8, before the stage-wise prediction is performed on the body-surface ECG using the at least two stages of pre-trained prediction models to produce the prediction result corresponding to the origin position of the VA, the method may further include:

determining locations of all QRS complexes and locations of QRS complexes during PVCs or VTs by detecting the body-surface ECG (which has preferably been denoised) using a pre-trained first machine learning model.

Through detecting the body-surface ECG (which has preferably been denoised) with the pre-trained first machine learning model, QRS complexes during PVCs or VTs can be quickly extracted, resulting in time savings and reducing the physician's work load. Moreover, the proneness to errors that may arise from manual detection of QRS complexes during PVCs or VTs can be avoided.

Figure 9:
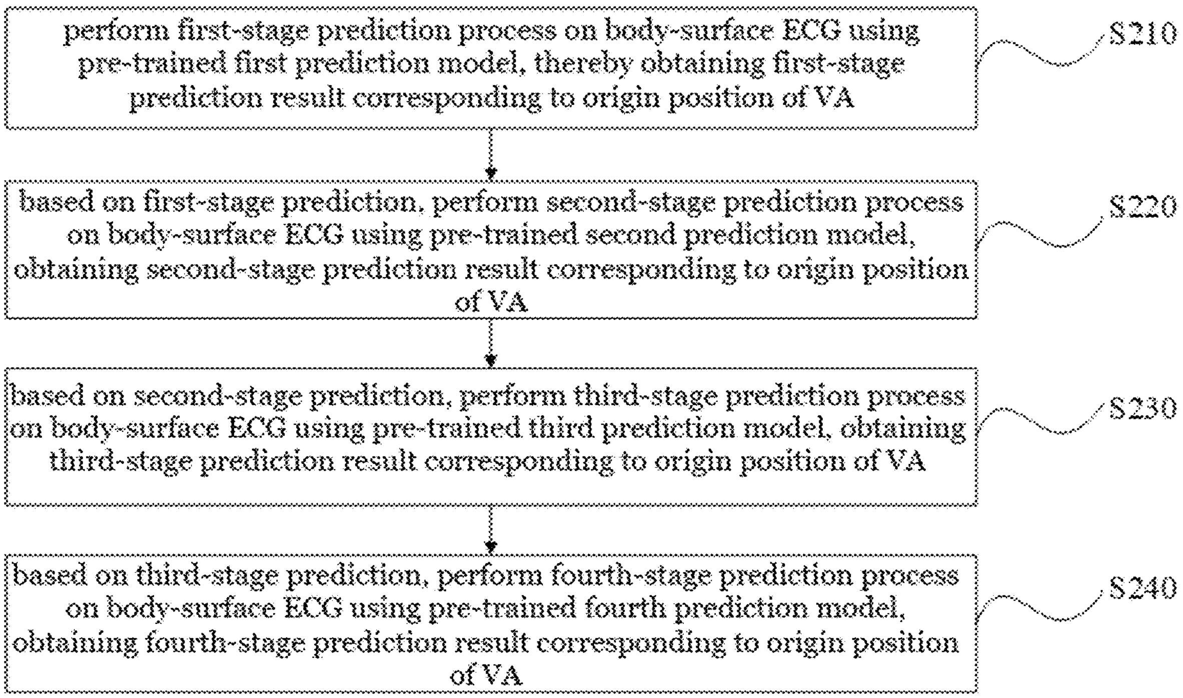
FIG. 9 is a schematic flowchart of a stage-wise prediction process according to an embodiment of the present invention.

Reference is additionally made to FIG. 9, a schematic flowchart of a stage-wise prediction process according to an embodiment of the present invention. As shown in FIG. 9, in step S200, performing stage-wise prediction on the body-surface ECG using the at least two stages of pre-trained prediction models to produce the prediction results corresponding to the origin position of the VA may include the steps of:

Step S210: performing a first-stage prediction process on the body-surface ECG (which has preferably been denoised) using a pre-trained first prediction model, thereby obtaining a first-stage prediction result corresponding to the origin position of the VA;

Step S220: based on the first-stage prediction, performing a second-stage prediction process on the body-surface ECG (which has preferably been denoised) using a pre-trained second prediction model, obtaining a second-stage prediction result corresponding to the origin position of the VA; and Step S230: based on the second-stage prediction, performing a third-stage prediction process on the body-surface ECG (which has preferably been denoised) using a pre-trained third prediction model, obtaining a third-stage prediction result corresponding to the origin position of the VA.

In this way, a three-stage prediction scheme is established with the first, second and third prediction models, in which the first-stage prediction obtained from the first prediction model serves as a basis for the next-stage prediction process (i.e., the second-stage prediction process) performed by the second prediction model, and the second-stage prediction obtained from the second prediction model serves as a basis for the next-stage prediction process (i.e., the third-stage prediction process) performed by the third prediction model. Finally, the third-stage prediction is obtained. This stage-wise prediction technique with incremental drilldown and refinement capabilities can provide a more accurate final prediction result corresponding to the origin position of the VA with substantially reduced prediction errors.

Additionally, as shown in FIG. 9, performing stage-wise prediction on the body-surface ECG using the at least two stages of pre-trained prediction models to produce the prediction results corresponding to the origin position of the VA in step S200 may further include the step of:

Step S240: based on the third-stage prediction, performing a fourth-stage prediction process on the body-surface ECG (which has preferably been denoised) using a pre-trained fourth prediction model, obtaining a fourth-stage prediction result corresponding to the origin position of the VA.

In this way, the third-stage prediction serves as a basis for the next-stage prediction process (i.e., the fourth-stage prediction process) performed by the fourth prediction model, obtaining a more detail VA origin site prediction. This can additionally facilitate the physician's fast identification of a specific target site for an ablation procedure and can further reduce the time required by the catheter ablation procedure.

Preferably, performing the first-stage prediction process on the body-surface ECG using the pre-trained first prediction model may include, based on the locations of the QRS complexes during the PVCs or VTs, performing the first-stage prediction process on the body-surface ECG (which has preferably been denoised) using the pre-trained first prediction model. Additionally, performing the second-stage prediction process on the body-surface ECG using the pre-trained second prediction model may include, based on the locations of the QRS complexes during the PVCs or VTs and the first-stage prediction, performing the second-stage prediction process on the body-surface ECG (which has preferably been denoised) using the pre-trained second prediction model. Additionally, performing the third-stage prediction process on the body-surface ECG using the pre-trained third prediction model based on the second-stage prediction may include, based on the locations of the QRS complexes during the PVCs or VTs and the second-stage prediction, performing the third-stage prediction process on the body-surface ECG (which has preferably been denoised) using the pre-trained third prediction model. Additionally, performing the fourth-stage prediction process on the body-surface ECG using the pre-trained fourth prediction model based on the third-stage prediction may include, based on the locations of the QRS complexes during the PVCs or VTs and the third-stage prediction, performing the fourth-stage prediction process on the body-surface ECG (which has preferably been denoised) using the pre-trained fourth prediction model.

Further, performing the first-stage prediction process on the body-surface ECG using the pre-trained first prediction model based on the locations of the QRS complexes during the PVCs or VTs may include:

extracting a first target ECG portion of a first target length from the body-surface ECG (which has preferably been denoised) according to the locations of the QRS complexes during the PVCs or VTs; and performing the first-stage prediction process on the first target ECG portion using the pre-trained first prediction model.

Performing the second-stage prediction process on the body-surface ECG using the pre-trained second prediction model based on the locations of the QRS complexes during the PVCs or VTs and the first-stage prediction may include:

extracting a second target ECG portion of a second target length from the body-surface ECG (which has preferably been denoised) according to the locations of the QRS complexes during the PVCs or VTs; and based on the first-stage prediction, performing the second-stage prediction process on the second target ECG portion using the pre-trained second prediction model, thereby obtaining the second-stage prediction result corresponding to the origin position of the VA.

Performing the third-stage prediction process on the body-surface ECG using the pre-trained third prediction model based on the locations of the QRS complexes during the PVCs or VTs and the second-stage prediction may include:

extracting a third target ECG portion of a third target length from the body-surface ECG (which has preferably been denoised) according to the locations of the QRS complexes during the PVCs or VTs; and based on the second-stage prediction, performing the third-stage prediction process on the third target ECG portion using the pre-trained third prediction model, thereby obtaining the third-stage prediction result corresponding to the origin position of the VA.

Performing the fourth-stage prediction process on the body-surface ECG using the pre-trained fourth prediction model based on the locations of the QRS complexes during the PVCs or VTs and the third-stage prediction may include:

extracting a fourth target ECG portion of a fourth target length from the body-surface ECG (which has preferably been denoised) according to the locations of the QRS complexes during the PVCs or VTs; and based on the third-stage prediction, performing the fourth-stage prediction process on the fourth target ECG portion using the pre-trained fourth prediction model, thereby obtaining the fourth-stage prediction result corresponding to the origin position of the VA.

Specifically, the first, second, third and fourth target lengths may be determined by a grid search performed by a pre-trained second machine learning model on numerous body-surface ECGs (which sampling frequencies have also been adjusted to the predetermined frequency, e.g., 2000 Hz), in which QRS complexes during PVCs or VTs have been labeled. According to the present invention, from the search performed by the pre-trained second machine learning model, optimal input lengths for the first, second, third and fourth prediction models can be obtained automatically. This can enhance prediction accuracy of each prediction model.

Training of the first prediction model will be described below to exemplify how the prediction models may be trained in accordance with the present invention. At first, a certain number of training samples may be obtained, which include body-surface ECG samples (preferably, 12-lead body-surface ECG) and origin site labels associated with the body-surface ECG samples (i.e., first-level anatomical regions encompassing VA origin sites). Subsequently, the body-surface ECG samples may be resampled (to tune the sampling frequency of each of them to the predetermined frequency, e.g., 2000 Hz) and denoised, and QRS complexes during PVCs or VTs in the denoised body-surface ECG samples may be then labeled by the pre-trained first machine learning model or manually. After that, a grid search may be performed in a predetermined candidate length range (e.g., 100 ms to 500 ms) at a predetermined step (e.g., 5 ms) by the pre-trained second machine learning model on the body-surface ECG samples, in which QRS complexes during PVCs or VTs have been labeled, thereby determining an optimal input length of the body-surface ECG portion for the first prediction model, i.e., the first target length. Thereafter, first target ECG portion samples of the first target length may be extracted from the body-surface ECG samples, and several predefined machine learning models (including K-Nearest Neighbors Regression, Support Vector Regression, Random Forest, Gradient Decision Tree, Gradient Boost Tree, Deep Learning, etc.) may be separately trained with the first target ECG portion samples and the associated origin site labels. The training of the various machine learning models may involve grid search iterations and may be ended after optimal hyperparameters have been obtained for the machine learning models. Finally, the trained machine learning models may be separately tested, and the one with the highest prediction accuracy may be selected as the first prediction model. Each of the second, third and fourth prediction models may be trained in a similar way, and for details of the training of these prediction models, reference can be made to the above description of the training of the first prediction model. However, in the training of the second prediction model, second-level anatomical regions encompassing VA origin sites may be taken as origin site labels associated with the body-surface ECG samples, and several predefined machine learning models may be separately trained with second target ECG portion samples of the second target length extracted from the body-surface ECG samples and with the associated origin site labels. In the training of the third prediction model, third-level anatomical regions encompassing VA origin sites may be taken as origin site labels associated with the body-surface ECG samples, and several predefined machine learning models may be separately trained with third target ECG portion samples of the third target length extracted from the body-surface ECG samples and with the associated origin site labels. In the training of the fourth prediction model, fourth-level anatomical regions encompassing VA origin sites may be taken as origin site labels associated with the body-surface ECG samples, and several predefined machine learning models may be separately trained with fourth target ECG portion samples of the fourth target length extracted from the body-surface ECG samples and with the associated origin site labels.

It is to be noted that in order to enhance prediction accuracy of the first, second, third and fourth prediction models, the training samples may be from real patient data, and the origin site labels may be from target sites in successful ablation cases.

In one exemplary embodiment, as shown in FIG. 8, the method may further include:

Displaying the prediction results corresponding to the origin position of the VA on a predefined 3D heart model, thereby generating a 3D prediction report.

Through displaying the prediction results corresponding to the origin position of the VA on the predefined 3D heart model, the predictions can be presented to a physician more intuitively, facilitating his/her reading.

Based on the same inventive concept, the present invention further provides a readable storage medium storing therein a computer program which, when executed by a processor, can implement all the steps in the method for predicting an origin position of a VA as defined above. For more details of this, reference can be made to the above description of the method, and further description thereof is omitted here. For details of advantages provided by the readable storage medium of the present invention, reference can be made to the above description of the benefits of the method, and further description thereof is omitted here.

According to embodiments of the present invention, the readable storage medium may be implemented by one of various computer-readable media, or any combination thereof. Each of the readable media may be a computer-readable signal medium or a computer-readable storage medium. The computer-readable storage medium may be, for example, but is not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. As used herein, the phase "computer-readable storage medium" may refer to any tangible medium that can contain, or store a program for use by or in connection with an instruction execution system, apparatus, or device.

The computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. The computer-readable signal medium may also be any computer-readable medium that is not a computer-readable storage medium and that can communicate, propagate, or transport a program for use by or in connection with an instruction execution system, apparatus, or device.

Computer program code for carrying out operations of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on a remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Based on the same inventive concept, the present invention further provides an electronic device including the system for predicting an origin position of a VA or the readable storage medium as defined above. For details of advantages provided by the electronic device of the present invention, reference can be made to the above description of the benefits of the system and method, and further description thereof is omitted here.

In summary, compared with the prior art, the system, electronic device and storage medium of the present invention have the advantages as follows: according to the present invention, stage-wise prediction can be carried out on an acquired body-surface ECG to be subjected to prediction by at least two stages of pre-trained prediction models. This enables a stage-wise drilldown search for an origin position of a VA, in which a large region encompassing the VA origin site may be first predicted, and a finer search may be then performed in the region to accurately drill down to a more detailed location encompassing the true VA origin site. In this way, the present invention is able to accurately predict the true VA origin site among all possible VA origin site candidates. This can not only help a physician to rapidly localize a specific target site to be ablated, but can greatly reduce the time required for the catheter ablation procedure, thus reducing unnecessary intervention mapping within the heart, reducing patient complications and providing a basis for assessment after the VA treatment.

It is to be noted that the devices and methods in the embodiments disclosed herein may also be implemented in other ways and the device embodiments described above are merely illustrative. For example, the flowcharts and block diagrams in the figures illustrate the architecture, functionality and operation of possible implementations of devices, methods, and computer program products according to various embodiments of the present invention. In this regard, each block in the flowcharts or block diagrams may represent a module, segment, or portion of instructions, which includes one or more executable instructions for implementing the specified logical function(s). It is to be also noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It is to be further noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

Further, the various functional modules in the embodiments herein may be integrated into a discrete component, or provided as separate modules. Alternatively, two or more such modules may be integrated into a discrete component.

The description presented above is merely that of a few preferred embodiments of the present invention and is not intended to limit the scope thereof in any sense. Any and all changes and modifications made by those of ordinary skill in the art based on the above teachings fall within the scope as defined in the appended claims. Apparently, those skilled in the art can make various modifications and variations to the present invention without departing from the spirit and scope thereof. Accordingly, the invention is intended to embrace all such modifications and variations if they fall within the scope of the appended claims and equivalents thereof.

What is claimed is:

1. A system for predicting an origin position of a ventricular arrhythmia (VA), comprising:

an acquisition module for acquiring a body-surface electrocardiogram (ECG) to be subjected to prediction;

a prediction module for performing stage-wise prediction on the body-surface ECG using at least two stages of pre-trained prediction models, thereby obtaining prediction results corresponding to the origin position of the VA; and a second pre-treatment module for denoising the body-surface ECG, wherein the second pre-treatment module is configured to remove high-frequency noise from the body-surface ECG by hierarchical time-frequency resolution and remove low-frequency noise from the body-surface ECG by non-linear fitting.

2. The system for predicting an origin position of a VA according to claim 1, wherein the prediction module comprises:

a first prediction sub-module for performing a first-stage prediction process on the body-surface ECG using a pre-trained first prediction model, thereby obtaining a first-stage prediction result corresponding to the origin position of the VA;

a second prediction sub-module for performing, based on the first-stage prediction, a second-stage prediction process on the body-surface ECG using a pre-trained second prediction model, thereby obtaining a second-stage prediction result corresponding to the origin position of the VA; and a third prediction sub-module for performing, based on the second-stage prediction, a third-stage prediction process on the body-surface ECG using a pre-trained third prediction model, thereby obtaining a third-stage prediction result corresponding to the origin position of the VA.

3. The system for predicting an origin position of a VA according to claim 2, wherein the prediction module further comprises:

a fourth prediction sub-module for performing, based on the third-stage prediction, a fourth-stage prediction process on the body-surface ECG using a pre-trained fourth prediction model, thereby obtaining a fourth-stage prediction result corresponding to the origin position of the VA.

4. The system for predicting an origin position of a VA according to claim 3, further comprising:

a QRS complex extraction module for determining locations of all QRS complexes and locations of QRS complexes during premature ventricular contractions (PVCs) or ventricular tachycardias (VTs) by detecting the body-surface ECG using a pre-trained first machine learning model, wherein:

the first prediction sub-module is configured to perform, based on the locations of the QRS complexes during the PVCs or VTs, the first-stage prediction process on the body-surface ECG using the pre-trained first prediction model, thereby obtaining the first-stage prediction result corresponding to the origin position of the VA;

the second prediction sub-module is configured to perform, based on the locations of the QRS complexes during the PVCs or VTs and the first-stage prediction, the second-stage prediction process on the body-surface ECG using the pre-trained second prediction model, thereby obtaining the second-stage prediction result corresponding to the origin position of the VA;

the third prediction sub-module is configured to perform, based on the locations of the QRS complexes during the PVCs or VTs and the second-stage prediction, the third-stage prediction process on the body-surface ECG using the pre-trained third prediction model, thereby obtaining the third-stage prediction result corresponding to the origin position of the VA; and the fourth prediction sub-module is configured to perform, based on the locations of the QRS complexes during the PVCs or VTs and the third-stage prediction, the fourth-stage prediction process on the body-surface ECG using the pre-trained fourth prediction model, thereby obtaining the fourth-stage prediction result corresponding to the origin position of the VA.

5. The system for predicting an origin position of a VA according to claim 4, wherein:

the first prediction sub-module comprises:

a first extraction unit for extracting a first target ECG portion of a first target length from the body-surface ECG according to the locations of the QRS complexes during the PVCs or VTs; and a first prediction unit for performing the first-stage prediction process on the first target ECG portion using the pre-trained first prediction model, thereby obtaining the first-stage prediction result corresponding to the origin position of the VA, and/or the second prediction sub-module comprises:

a second extraction unit for extracting a second target ECG portion of a second target length from the body-surface ECG according to the locations of the QRS complexes during the PVCs or VTs; and a second prediction unit for performing, based on the first-stage prediction, the second-stage prediction process on the second target ECG portion using the pre-trained second prediction model, thereby obtaining the second-stage prediction result corresponding to the origin position of the VA, and/or the third prediction sub-module comprises:

a third extraction unit for extracting a third target ECG portion of a third target length from the body-surface ECG according to the locations of the QRS complexes during the PVCs or VTs; and a third prediction unit for performing, based on the second-stage prediction, the third-stage prediction process on the third target ECG portion using the pre-trained third prediction model, thereby obtaining the third-stage prediction result corresponding to the origin position of the VA, and/or the fourth prediction sub-module comprises:

a fourth extraction unit for extracting a fourth target ECG portion of a fourth target length from the body-surface ECG according to the locations of the QRS complexes during the PVCs or VTs; and a fourth prediction unit for performing, based on the third-stage prediction, the fourth-stage prediction process on the fourth target ECG portion using the pre-trained fourth prediction model, thereby obtaining the fourth-stage prediction result corresponding to the origin position of the VA.

6. The system for predicting an origin position of a VA according to claim 1, further comprising:

a first pre-treatment module for determining whether a sampling frequency of the body-surface ECG is equal to a predetermined frequency and, if not, resampling the body-surface ECG.

7. The system for predicting an origin position of a VA according to claim 1, further comprising:

a report generation module for displaying the prediction results corresponding to the origin position of the VA on a predefined three-dimensional (3D) heart model, thereby generating a 3D prediction report.

8. An electronic device comprising the system of claim 1 and a non-transitory readable storage medium, the non-transitory readable storage medium storing therein a computer program, wherein the computer program, when executed by a processor, implements steps of:

acquiring a body-surface electrocardiogram (ECG) to be subjected to prediction; and performing stage-wise prediction on the body-surface ECG using at least two stages of pre-trained prediction models, thereby obtaining prediction results corresponding to the origin position of the VA; and denoising the body-surface ECG, wherein denoising the body-surface ECG comprises: removing high-frequency noise from the body-surface ECG by hierarchical time-frequency resolution and removing low-frequency noise from the body-surface ECG by non-linear fitting.

9. A non-transitory readable storage medium, storing therein a computer program, wherein the computer program, when executed by a processor, implements steps of:

acquiring a body-surface electrocardiogram (ECG) to be subjected to prediction;

performing stage-wise prediction on the body-surface ECG using at least two stages of pre-trained prediction models, thereby obtaining prediction results corresponding to the origin position of the VA; and denoising the body-surface ECG, wherein denoising the body-surface ECG comprises: removing high-frequency noise from the body-surface ECG by hierarchical time-frequency resolution and removing low-frequency noise from the body-surface ECG by non-linear fitting.

10. The non-transitory readable storage medium according to claim 9, wherein performing the stage-wise prediction on the body-surface ECG using the at least two stages of pre-trained prediction models and thereby obtaining the prediction results corresponding to the origin position of the VA comprises:

performing a first-stage prediction process on the body-surface ECG using a pre-trained first prediction model, thereby obtaining a first-stage prediction result corresponding to the origin position of the VA;

performing, based on the first-stage prediction, a second-stage prediction process on the body-surface ECG using a pre-trained second prediction model, thereby obtaining a second-stage prediction result corresponding to the origin position of the VA; and performing, based on the second-stage prediction, a third-stage prediction process on the body-surface ECG using a pre-trained third prediction model, thereby obtaining a third-stage prediction result corresponding to the origin position of the VA.

11. The non-transitory readable storage medium according to claim 10, wherein performing the stage-wise prediction on the body-surface ECG using the at least two stages of pre-trained prediction models and thereby obtaining the prediction results corresponding to the origin position of the VA further comprises:

performing, based on the third-stage prediction, a fourth-stage prediction process on the body-surface ECG using a pre-trained fourth prediction model, thereby obtaining a fourth-stage prediction result corresponding to the origin position of the VA.

12. The non-transitory readable storage medium according to claim 11, wherein the computer program, when executed by the processor, further implements a step of:

determining locations of all QRS complexes and locations of QRS complexes during premature ventricular contractions (PVCs) or ventricular tachycardias (VTs) by detecting the body-surface ECG using a pre-trained first machine learning model, performing the first-stage prediction process on the body-surface ECG using the pre-trained first prediction model comprises:

performing, based on the locations of the QRS complexes during the PVCs or VTs, the first-stage prediction process on the body-surface ECG using the pre-trained first prediction model;

performing the second-stage prediction process on the body-surface ECG using the pre-trained second prediction model comprises:

performing, based on the locations of the QRS complexes during the PVCs or VTs and the first-stage prediction, the second-stage prediction process on the body-surface ECG using the pre-trained second prediction model;

performing the third-stage prediction process on the body-surface ECG based on the second-stage prediction using the pre-trained third prediction model comprises:

performing, based on the locations of the QRS complexes during the PVCs or VTs and the second-stage prediction, the third-stage prediction process on the body-surface ECG using the pre-trained third prediction model; and performing the fourth-stage prediction process on the body-surface ECG based on the third-stage prediction using the pre-trained fourth prediction model comprises:

performing, based on the locations of the QRS complexes during the PVCs or VTs and the third-stage prediction, the fourth-stage prediction process on the body-surface ECG using the pre-trained fourth prediction model.

13. The non-transitory readable storage medium according to claim 12, wherein:

performing the first-stage prediction process on the body-surface ECG using the pre-trained first prediction model based on the locations of the QRS complexes during the PVCs or VTs comprises: extracting a first target ECG portion of a first target length from the body-surface ECG according to the locations of the QRS complexes during the PVCs or VTs; and performing the first-stage prediction process on the first target ECG portion using the pre-trained first prediction model, and/or performing the second-stage prediction process on the body-surface ECG using the pre-trained second prediction model based on the locations of the QRS complexes during the PVCs or VTs and the first-stage prediction comprises:

extracting a second target ECG portion of a second target length from the body-surface ECG according to the locations of the QRS complexes during the PVCs or VTs; and performing, based on the first-stage prediction, the second-stage prediction process on the second target ECG portion using the pre-trained second prediction model, thereby obtaining the second-stage prediction result corresponding to the origin position of the VA, and/or performing the third-stage prediction process on the body-surface ECG using the pre-trained third prediction model based on the locations of the QRS complexes during the PVCs or VTs and the second-stage prediction comprises:

extracting a third target ECG portion of a third target length from the body-surface ECG according to the locations of the QRS complexes during the PVCs or VTs; and performing, based on the second-stage prediction, the third-stage prediction process on the third target ECG portion using the pre-trained third prediction model, thereby obtaining the third-stage prediction result corresponding to the origin position of the VA, and/or performing the fourth-stage prediction process on the body-surface ECG using the pre-trained fourth prediction model based on the locations of the QRS complexes during the PVCs or VTs and the third-stage prediction comprises:

extracting a fourth target ECG portion of a fourth target length from the body-surface ECG according to the locations of the QRS complexes during the PVCs or VTs; and performing, based on the third-stage prediction, the fourth-stage prediction process on the fourth target ECG portion using the pre-trained fourth prediction model, thereby obtaining the fourth-stage prediction result corresponding to the origin position of the VA.

14. The non-transitory readable storage medium according to claim 9, wherein the computer program, when executed by the processor, further implements a step of:

displaying the prediction results corresponding to the origin position of the VA on a predefined three-dimensional (3D) heart model, thereby generating a 3D prediction report.

15. The non-transitory readable storage medium according to claim 9, wherein the computer program, when executed by the processor, further implements a step of:

determining whether a sampling frequency of the body-surface ECG is equal to a predetermined frequency and, if not, resampling the body-surface ECG.

* * * * *